United States Patent [19]

Lesieur et al.

[11] Patent Number: 4,960,778
[45] Date of Patent: Oct. 2, 1990

[54] NEW BENZOXAZOLINONE COMPOUNDS

[75] Inventors: Daniel Lesieur, Gondecourt; Nourddine Abdellatifi, Wattignies; Hocine Aichaoui, Loos; Jacqueline Bonnet, Paris, all of France

[73] Assignee: ADIR Et Cie, Neuilly-sur-Seine, France

[21] Appl. No.: 416,595

[22] Filed: Oct. 3, 1989

[30] Foreign Application Priority Data

Oct. 4, 1988 [FR] France ................... 88 12945

[51] Int. Cl.$^5$ ............... A61K 31/495; C07D 413/06; C07D 413/12
[52] U.S. Cl. .................................. 514/253; 544/368
[58] Field of Search ........................ 544/368; 514/253

[56] References Cited

U.S. PATENT DOCUMENTS

| 3,944,551 | 3/1976 | Regnier et al. | 544/368 |
| 4,558,060 | 12/1985 | Caignard et al. | 514/375 |

FOREIGN PATENT DOCUMENTS

| 747274 | 8/1970 | Belgium | 544/368 |
| 2429253 | 1/1976 | Fed. Rep. of Germany . | |
| 8020861 | 9/1980 | France . | |
| 8219812 | 11/1982 | France . | |
| 46-04378 | 2/1971 | Japan | 544/368 |
| 46-18993 | 5/1971 | Japan | 544/368 |
| 01186 | 4/1982 | World Int. Prop. O. | 544/368 |

OTHER PUBLICATIONS

Mentrup et al, CA 84-135683e (1976).

Primary Examiner—Cecilia Shen
Attorney, Agent, or Firm—Gordon W. Hueschen

[57] ABSTRACT

Compounds of the general formula (I):

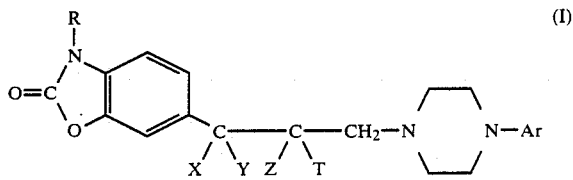

in which:
X denotes a hydrogen atom,
Y denotes a hydrogen atom or a hydroxyl group or alternatively X and Y together denote an oxygen atom,
T denotes a hydrogen atom or a lower alkyl group,
Z denotes a hydrogen atom or alternatively Z forms a π bond with Y, in which case X denotes a hydrogen atom,
R denotes a hydrogen atom or a lower alkyl group,
Ar denotes an aryl or heteroaryl or (lower alkyl)aryl group, such as pyrimidinyl, optionally substituted with a halogen atom, or a lower alkyloxy or alkyl group, themselves optionally substituted with one or more halogen atoms, their enantiomers, epimers and diastereoisomers, as well as their addition salts with a pharmaceutically acceptable acid.

12 Claims, No Drawings

NEW BENZOXAZOLINONE COMPOUNDS

The present invention relates to new benzoxazolinone compounds, to their preparation and to pharmaceutical compositions containing them.

Many benzoxazolinone compounds have been described in therapeutics as possessing a wide variety of pharmacological activities. French Patent No. 73/23,280 describes 6-acylbenzoxazolinones as analgesics. French Patent No. 80/20,861 describes, in particular, 6-(2-aminoethyl)benzoxazolinones and 6-(aminoacetyl)benzoxazolinones which are usable in the treatment of arterial hypertension as well as in that of painful syndromes. French Patent No. 82/19,812 describes 6-(2-aminoethyl)benzoxazolinones which are usable in therapy in the treatment of sleep disorders and character and behavioral disorders.

The Applicant has now discovered benzoxazolinone compounds endowed with an analgesic activity which is devoid of anti-inflammatory activity, of a markedly more advantageous level than that of the compounds described in French Patent Nos. 73/23,280 and 80/20,861. The compounds of the present invention are, in effect, endowed with a high-level pure analgesic activity. In point of fact, most non-morphinic analgesic substances known to date also possess anti-inflammatory activity (for example salicyl derivatives, pyrazole derivatives, etc.), and they consequently intervene in the processes occurring in inflammation. These processes involve a very large number of chemical mediators (prostaglandins, thromboxane A2, etc.); multifarious side effects accordingly ensue, the best known of which are attack of the gastric mucosa with the possibility of ulcers and inhibition of platelet aggregation with disorders of coagulation. Apart from the disturbances they cause, these concomitant effects prohibit the use of these products in many subjects who are especially sensitive to them. Being devoid of all anti-inflammatory activity, the compounds of the present invention do not interact with the mediators of inflammation and are hence devoid of the side effects mentioned above. This feature, combined, in the case of a number of the compounds, with a complete absence of toxicity and a high level of activity, renders some compounds of the present invention usable as analgesics much more safely and without the restrictions in use customarily known for the great majority of these products.

More specifically, the invention relates to the compounds of the general formula (I):

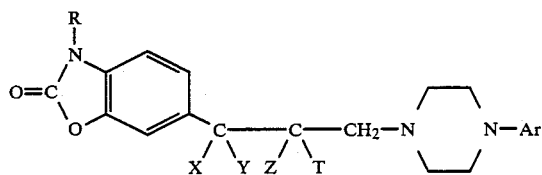

in which:
X denotes a hydrogen atom,
Y denotes a hydrogen atom or a hydroxyl group or alternatively X and Y together denote an oxygen atom,
T denotes a hydrogen atom or a lower alkyl group,
Z denotes a hydrogen atom or alternatively Z forms a $\pi$ bond with Y, in which case X denotes a hydrogen atom,
R denotes a hydrogen atom or a lower alkyl group,
Ar denotes an aryl or heteroaryl or (lower alkyl)aryl group, optionally substituted with a halogen atom, or a lower alkyloxy or alkyl group, themselves optionally substituted with one or more halogen atoms, their enantiomers, epimers and diastereoisomers, as well as their addition salts with a pharmaceutically acceptable acid.

Among acids which may be used for salifying compounds of the general formula (I), hydrochloric, sulfuric, phosphoric, tartaric, malic, maleic, fumaric, oxalic, methanesulfonic, ethanesulfonic, camphoric and citric acids, and the like, may be mentioned without implied limitation.

The invention also encompasses two processes for the production of the compounds of the formula (I).

Depending on the compounds of the invention which it is desired to obtain, it may, in effect, be advantageous to use either one process or the other.

The first process for preparing the compounds of the formula (I), which is especially advantageous for the production of the compounds of formula (I) in which X, Y and Z each denote a hydrogen atom, can nevertheless be applied for the compounds in which X, Y and Z have other meanings, and employs as starting material a derivative of the formula (II):

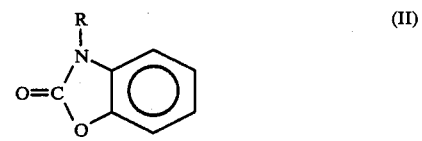

in which R has the same meaning as in the formula (I), the compounds being obtained, for example, by the reaction of ortho-aminophenol with urea followed, when R is other than H, by an alkylation on the nitrogen, which compound is subjected to the action of an acid chloride of the formula (III):

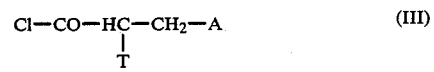

in which T has the same meaning as in the formula (I), A denoting a halogen atom, or alternatively of the corresponding acid anhydride, in the presence of aluminum chloride in dimethylformamide according to the conditions of THYES et al. (J. Med. Chem. 1983, 26, 6, 800–807), to obtain a compound of the formula (IV):

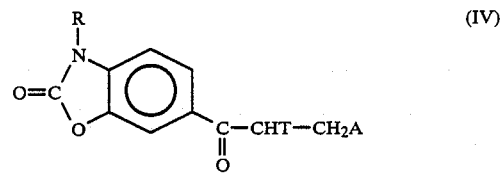

in which R and T have the same meaning as in the formula (I) and A has the same meaning as in the formula (III), which, if so desired, is subjected to reduction with a trialkylsilane in an acid medium according to the conditions described by WEST et al. (J. Org. Chem. 1973, 38, (15), 2675–2681), to lead to a compound of the formula (V):

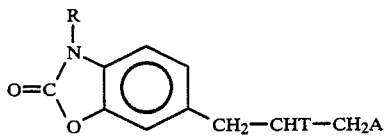
(V)

in which R and T have the same meaning as in the formula (I) and A has the same meaning as in the formula (III), the compound of the formula (IV) or the compound of the formula (V), depending on the formula of the compound of the formula (I) which it is desired to obtain, then being subjected to the action of a 1-arylpiperazine of the formula (VI):

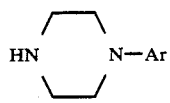
(VI)

in which Ar has the same meaning as in the formula (I), in a solvent preferably chosen from acetone, acetonitrile, ethyl acetate, lower aliphatic alcohol, dioxane, benzene and toluene, at a temperature between room temperature and the boiling point of the chosen solvent, in the presence of an excess of the chosen amine or of a trapping agent for the hydracid formed, such as triethylamine, to lead to a compound of the formula (I/A):

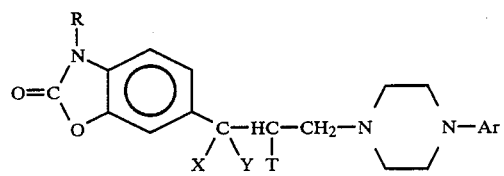
(I/A)

in which, depending on whether the starting material used is a compound of the formula (IV) or (V), X and Y together denote an oxygen atom, or alternatively X and Y both simultaneously denote a hydrogen atom, R, Ar and T having the same meaning as in the formula (I), which, if so desired, is salified with a pharmaceutically acceptable acid or which can, when X and Y together denote an oxygen atom, if so desired, be subjected either to a hydrogenating agent chosen from an alkali metal mixed hydride such as, for example, sodium borohydride, or an alkali metal mixed cyanohydride such as sodium cyanoborohydride, preferably in a lower aliphatic alcohol medium, to lead to a derivative of the formula (I/B)—predominantly in the threo configuration when T does not denote a hydrogen atom:

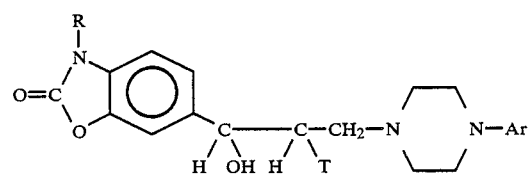
(I/B)

a special case of the compound of formula (I) in which:
R, T and Ar have the same meaning as in the compound of the formula (I), X here denoting a hydrogen atom,
Y a hydroxyl group and Z a hydrogen atom,
the isomers of which are separated if so desired, and/or which is salified with a pharmaceutically acceptable acid, or alternatively to catalytic hydrogenation, with heating and under pressure in a solvent chosen from lower aliphatic alcohol or dioxane, to lead to a derivative of the formula (I/B)—essentially in the erythro configuration when T does not denote a hydrogen atom—the isomers of which are separated if so desired, and which is salified, where appropriate, with a pharmaceutically acceptable acid, which derivative of the formula (I/B), irrespective of the process according to which it has been obtained, can, if so desired, be treated with a dehydrating agent, preferably chosen from hydracids, to lead to a derivative of the formula (I/C):

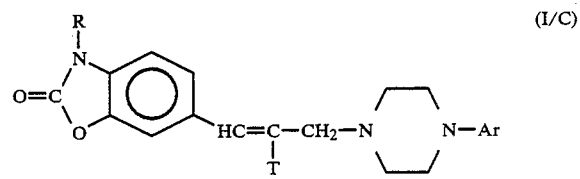
(I/C)

predominantly in the form of the trans isomer, a special case of compounds of formula (I) in which:
R, T and Ar have the same meaning as in the compounds of the formula (I),
X here denoting a hydrogen atom,
Z forming a $\pi$ bond with Y,
the cis/trans isomers of which are separated, if so desired, by a familiar technique such as chromatography on a silica column or crystallization, and which, if so desired, may be salified with a pharmaceutically acceptable acid.

The second process for the production of the compounds of the present invention is inapplicable for the compounds for which R denotes a hydrogen atom.

In this second process, a compound of the formula (II), obtained as stated above:

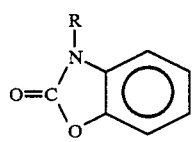
(II)

in which R denotes a lower alkyl group, is acylated with an acid of the formula (VII):

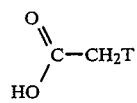
(VII)

in which T has the same meaning as in the formula (I), or the corresponding chloride or anhydride of the acid, according to the conditions described in French Patent No. 73/23,280, to obtain a compound of the formula (VIII):

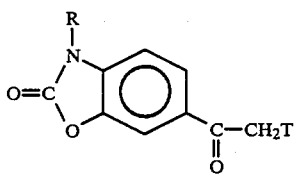
(VIII)

in which R denotes a lower alkyl group and T has the same meaning as in the formula (I), which is then treated either according to the conditions of the Mannich reaction, which are well known to those versed in the art, in the presence of trioxymethylene and of the chosen arylpiperazine of the formula (VI):

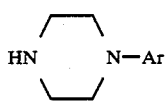
(VI)

in which Ar has the same meaning as in the formula (I), to obtain a compound of the formula (I/A1):

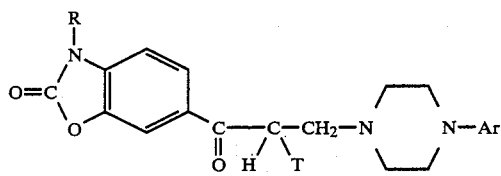
(I/A1)

a special case of the compounds of formulae (I/A) and (I) in which:

R denotes a lower alkyl group, and T and Ar have the same meaning as in the formula (I), X and Y here simultaneously denoting an oxygen atom and Z a hydrogen atom, or alternatively with bis(dimethylamino)methane in an acetic anhydride medium to obtain a product of the general formula (IX):

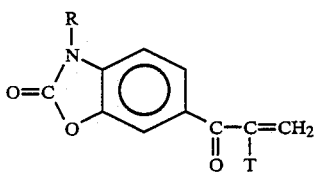
(IX)

in which:

T has the same meaning as in the formula (I) and R denotes a lower alkyl group, which is treated with an amine of the formula (VI), in a polar solvent at a temperature between room temperature and the boiling point of the reaction medium, to lead to a compound of formula (I/A1) defined above, which, when T does not denote a hydrogen atom, can, if so desired, be separated into its isomers, which are salified, if so desired, with a pharmaceutically acceptable acid, and which can if so desired, be subjected either, preferably in a lower aliphatic alcohol medium, to a hydrogenating agent, preferably an alkali metal mixed hydride or an alkali metal mixed cyanohydride such as, for example, sodium borohydride or sodium cyanoborohydride, to lead to a compounds of the formula (I/B), predominantly in the threo configuration (when T does not denote a hydrogen atom):

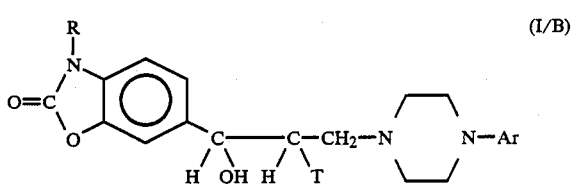
(I/B)

a special case of the compounds of the formula (I) in which:

R, T and Ar have the same meaning as in the de compounds of the formula (I),

X here denoting a hydrogen atom,

Y a hydroxyl group and Z a hydrogen atom, the isomers of which are separated if so desired, and which may be salified with a pharmaceutically acceptable acid, or alternatively to catalytic hydrogenation, in a solvent chosen from lower aliphatic alcohol or dioxane, to lead to a derivative of the formula (I/B), essentially in the erythro configuration—when T does not denote a hydrogen atom—the isomers of which are separated if so desired, and which is salified, where appropriate, with a pharmaceutically acceptable acid, which compound of the formula (I/B), is, where appropriate, subjected to a dehydrating agent preferably chosen from hydracids, to lead to a compound of the formula (I/C), predominantly in the form of trans isomers:

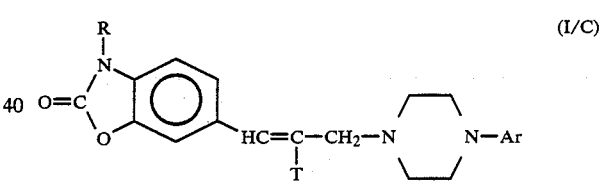
(I/C)

a special case of compounds of the formula (I) in which:

R, T and Ar have the same meaning as in the compounds of the formula (I),

X here denoting a hydrogen atom,

Z forming a π bond with Y, the cis/trans isomers of which are separated, if so desired, by a familiar technique such as chromatography on a silica column or crystallization, and which is salified, if so desired, with a pharmaceutically acceptable acid, which, if so desired, is subjected to a catalytic hydrogenation reaction, preferably at room temperature and atmospheric pressure and in the presence of Raney nickel in a lower aliphatic alcohol or dioxane medium, to obtain a compound of the formula (I/D):

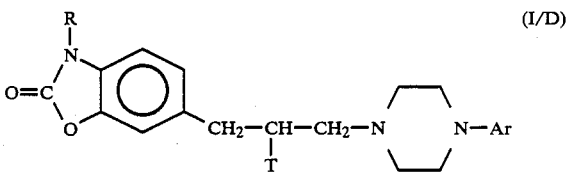
(I/D)

in which:

R, T and Ar have the same meaning as in the formula (I),

X, Y and Z each simultaneously denoting a hydrogen atom, the isomers of which are separated, where appropriate, when T does not denote a hydrogen atom, and which is optionally salified with a pharmaceutically acceptable acid.

The compounds of the formula (I/D) may also be obtained from the compounds of the formula (IX):

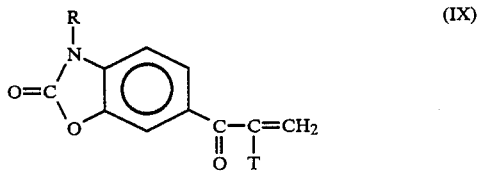

in which:

R and T have the same meaning as in the formula (I), which are treated with a hydracid to obtain a compound of the formula (IV):

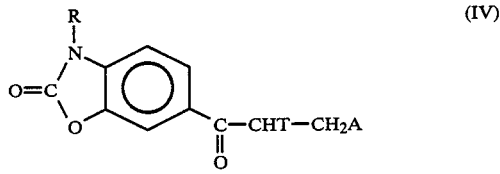

in which R and T have the same meaning as in the formula (I) and A the same meaning as in the formula (III), the isomers of which are separated, if so desired, when T does not denote a hydrogen atom, which is subjected to reduction with a trialkylsilane in an acid medium according to the conditions described by WEST et al. (J. Org. Chem. 1973, 38, (15), 2675–2681), to lead to a derivative of the formula (V):

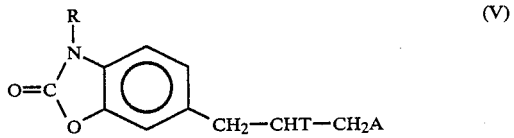

in which R and T have the same meaning as in the formula (I) and A the same meaning as in the formula (III), which is subjected to the action of a 1-arylpiperazine of the formula (VI):

in which Ar has the same meaning as in the formula (I), in a solvent preferably chosen from acetone, acetonitrile, ethyl acetate, lower aliphatic alcohol, dioxane, benzene and toluene, at a temperature between room temperature and the boiling point of the chosen solvent, in the presence of an excess of the chosen amine or of a trapping agent for the hydracid formed, such as triethylamine, to lead to a compound of the formula (I/D) designated above, which is salified, if so desired, with a pharmaceutically acceptable acid.

The compounds of formula (I) possess advantageous pharmacological properties.

In particular, these compounds have evinced an advantageous analgesic activity.

A pharmacological study of the compounds of the invention showed, in effect, that they were of low toxicity, endowed with a pure analgesic activity and hence devoid of drawbacks inherent in most non-morphinic compounds exhibiting this activity (ulcerogenic action on the mucosae, interference with coagulation, etc.). This spectrum of activity hence renders the compounds of the present invention advantageous in a number of indications such as rheumatic pain, neuralgia, lumbosciatic pain, cervicobrachial neuralgia, pain associated with trauma such as sprains, fractures, dislocations, post-traumatic pain, postoperative pain, dental pain, neurological pain such as facial neuralgia, visceral pain such as nephritic colic, pain associated with dysmenorrhea and proctological surgery, pain of the ENT region, pancreatitis, various pains, headache, cancer pain, etc.

The subject of the present invention is also pharmaceutical compositions containing the products of the formula (I), alone or in combination with one or more pharmaceutically acceptable, non-toxic, inert vehicles or excipients.

Among pharmaceutical compositions according to the invention, there may be mentioned, more especially, those which are suitable for oral, parenteral and nasal administration, simple or sugar-coated tablets, sublingual tablets, sachets, packets, gelatin capsules, sublingual preparations, pills, suppositories, creams, ointments, skin gels, and the like.

The appropriate dosage varies according to the patient's age and weight, the administration route, the nature of the therapeutic indication and any associated treatments, and ranges between 1 centigram and 4 grams per 24 hours.

The examples which follow illustrate the invention and in no way limit the latter.

The $^1$H nuclear magnetic resonance spectra were recorded using TMS as internal reference. The solvent used is deuterochloroform except where otherwise stated.

The infrared spectra were run using a potassium bromide disk containing approximately 1% of the test product.

EXAMPLE 1

3-METHYL-6-{3-[4-(3-TRIFLUOROMETHYLPHENYL)-1-PIPERAZINYL]-1-OXOPROPYL} BENZOXAZOLINONE 0.03 mole of 6-acetyl-3-methylbenzoxazolinone, obtained as described in French Patent No. 73/23,280, and 0.045 mole of 1-(3-trifluoromethylphenyl) piperazine hydrochloride are dissolved with magnetic stirring in 150 cm³ of ethanol in a 250 cm³ ground-necked flask equipped with a reflux condenser. 0.045 mole of trioxymethylene is added and the mixutre is acidified with hydrochloric acid and heated to reflux for 72 hours. The precipitate formed is drained, washed with acetone, suspended in water and alkalinized with sodium hydroxide. The mixture is extracted several times with chloroform and the organic phases are driver over calcium chloride, filtered and evaporated on a water bath under vacuum. The residue is recrystallized in ethanol.

Yield: 70%.

Melting point: 137° C.

Spectral characteristics:
Infrared: 1770 cm$^{-1}$:$\nu$ CO (O—CO—N); 1665 cm$^{-1}$:$\nu$ CO (acyl).
Nuclear magnetic resonance: $\delta$=2.70 ppm, complex, 6H, CH$_2$—N and piperazine; $\delta$=3.20 ppm, complex, 6H, CO—CH$_2$ and piperazine; $\delta$=3.45 ppm, singlet, 3H, CH$_3$; N—CH$_3$.

EXAMPLE 2

3-METHYL-6-{3-[4-(2-METHOXYPHENYL)-1-PIPERAZINYL]-1-OXOPROPYL}BENZOXAZOLINONE

Using the procedure described in Example 1, but replacing 1-(3-trifluoromethylphenyl)piperazine by 1-(2-methoxyphenyl)piperazine, the product of the title is obtained.
Yield: 70%.
Melting point: 152° C.
Spectral characteristics:
Infrared: 1760 cm$^{-1}$:$\nu$ CO (O—CO—N); 1670 cm$^{-1}$:$\nu$ CO (acyl).
Nuclear magnetic resonance (solvent CDCl$_3$): $\delta$=2.80 ppm, complex, 6H, CH$_2$—N and piperazine; $\delta$=3.15 ppm, complex, 6H, CO—CH$_2$ and piperazine; $\delta$=3.50 ppm, singlet, 3H, N—CH$_3$; $\delta$=3.90, singlet, 3H, OCH$_3$.

EXAMPLE 3

3-METHYL-6-{3-[4-(4-FLUOROPHENYL)-1-PIPERAZINYL]-1-OXOPROPYL}BENZOXAZOLINONE

Using the procedure described in Example 1, but replacing 1-(3-trifluoromethylphenyl)piperazine by 1-(4-fluorophenyl)piperazine, the expected product is obtained.
Yield: 70%.
Melting point: 149° C.
Spectral characteristics:
Infrared: 1770 cm$^{-1}$:$\nu$ CO (O—CO—N); 1665 cm$^{-1}$:$\nu$ CO (acyl).
Nuclear magnetic resonance (solvent CDCl$_3$): $\delta$=2.75 ppm, complex, 6H, CH$_2$—N and piperazine; $\delta$=3.15 ppm, complex, 6H, CO—CH$_2$ and piperazine; $\delta$=3.45 ppm, singlet, 3H, N—CH$_3$;

EXAMPLE 4

3-METHYL-6-{3-[4-(2-PYRIMIDINYL)-1-PIPERAZINYL]-1-OXOPROPYL}BENZOXAZOLINONE

Using the procedure described in Example 1, but replacing 1-(3-trifluoromethylphenyl)piperazine by 1-(2-pyrimidinyl)piperazine, the product of the title is obtained.

EXAMPLE 5

3-METHYL-6-{3-[4-(3-TRIFLUOROMETHYLPHENYL)-1-PIPERAZINYL]-1-HYDROXYPROPYL}BENZOXAZOLINONE

STAGE A: 3-Methyl-6-{3-[4-(3-trifluoromethylphenyl)-1-piperazinyl]-1-oxopropyl}benzoxazolinone
See Example 1.
STAGE B: 3-Methyl-6-{3-[4-(3-trifluoromethylphenyl)-1-piperazinyl]-1-hydroxypropyl}benzoxazolinone
0.01 mole of 3-methyl-6-{3-[4-(3-trifluoromethylphenyl)-1-piperazinyl]-1-oxopropyl}benzoxazolinone is dissolved in 200 cm$^3$ of methanol in a 250-cm$^3$ flask equipped with a magnetic stirrer. 0.02 mole of sodium borohydride is added very slowly and with stirring. Stirring is maintained for 4 hours at room temperature. The reaction medium is evaporated on a water bath under vacuum. The residue is taken up with water and extracted several times with chloroform. The extracts are filtered and evaporated to dryness on a water bath under vacuum. The product is recrystallized in ethanol.
Yield: 75%.
Melting point: 139° C.
Spectral characteristics:
Infrared: 3240 cm$^{-1}$:$\nu$ OH (secondary alcohol); 1750 cm$^{-1}$:$\nu$ CO (O—CO—N).
Nuclear magnetic resonance: $\delta$=1.83 ppm, complex, 2H, CHOH—CH$_2$—CH$_2$; $\delta$=2.75 ppm, complex, 6H, CH$_2$—N and piperazine; $\delta$=3.35 ppm, complex, 7H, N—CH$_3$ and piperazine; $\delta$=4.95 ppm, triplet, 1H, CHOH, J=5.6 Hz.

EXAMPLE 6

3-METHYL-6-{3-[4-(2-METHOXYPHENYL)-1-PIPERAZINYL]-1-HYDROXYPROPYL}BENZOXAZOLINONE

Using the procedure described in Example 5, but replacing 3-methyl-6-{3-[4-(3-trifluoromethylphenyl)-1-piperazinyl]-1-oxopropyl}benzoxazolinone by 3-methyl-6-{3-[4-(2-methoxyphenyl)-1-piperazinyl]-1-oxopropyl}benzoxazolinone, the product of the title is obtained.
Melting point: 133°–134° C.
Spectral characteristics:
Infrared: 3140 cm$^{-1}$:$\nu$ OH (secondary alcohol); 1770 cm$^{-1}$:$\nu$ CO (O—CO—N).
Nuclear magnetic resonance: $\delta$=1.88 ppm, complex, 2H, CHOH, CH$_2$—CH$_2$; $\delta$=2.80 ppm, complex, 6H, CH$_2$—N and piperazine; $\delta$=3.15 ppm, triplet, 4H, piperazine, J=4.7 Hz; $\delta$=3.38 ppm, singlet, 3H, N—CH$_3$; $\delta$=3.85 ppm, singlet, 3H, OCH$_3$; $\delta$=4.96 ppm, triplet, 1H, CH—OH.

EXAMPLE 7

3-METHYL-6-{3-[4-(4-FLUOROPHENYL)-1-PIPERAZINYL]-1-HYDROXYPROPYL}BENZOXAZOLINONE

Using the procedure described in Example 5, but replacing 3-methyl-6-{3-[4-(3-trifluoromethylphenyl)-1-piperazinyl]-1-oxopropyl}benzoxazolinone by 3-methyl-6-{3-[4-(4-fluorophenyl)-1-piperazinyl]-1-oxopropyl} benzoxazolinone, the product of the title is obtained.
Melting point: 150°–151° C.
Spectral characteristics:
Infrared: 3450 cm$^{-1}$:$\nu$ OH (secondary alcohol); 1745 cm$^{-1}$:$\nu$ CO (O—CO—N).
Nuclear magnetic resonance: $\delta$=1.83 ppm, complex, 2H, CH$_2$—CH$_2$—N; $\delta$=2.70 ppm, complex, 6H, CH$_2$—N and piperazine; $\delta$=3.18 ppm, triplet, 4H, piperazine, J=4.6 Hz; $\delta$=3.37 ppm, singlet, 3H, N—CH$_3$; $\delta$=4.96 ppm, triplet, 1H, CH—OH.

EXAMPLE 8

3-METHYL-6-{3-[4-(3-TRIFLUOROMETHYLPHENYL)-1-PIPERAZINYL]-1-PROPENYL}BENZOXAZOLINONE

STAGE A: 3-Methyl-6-{3-[4-(3-trifluoromethylphenyl)-1-piperazinyl]-1-hydroxypropyl}benzoxazolinone Obtained in Example 5.

STAGE B: 3-Methyl-6-{3-[4-(3-trifluoromethylphenyl)-1-piperazinyl]-1-propenyl}benzoxazolinone 0.015 mole of 3-methyl-6-{3-[4-(3-trifluoromethylphenyl)-1-piperazinyl]-1-hydroxypropyl}benzoxazolinone is dissolved in 47% strength hydrobromic acid in a 250-cm³ flask, and the solution is stirred at room temperature for 2 hours. The precipitate obtained is drained, washed with acetone, suspended in water and alkalinized with sodium hydroxide. The mixture is extracted several times with chloroform, the organic phases are combined and dried over calcium chloride, filtered and evaporated to dryness on a water bath under vacuum and the base is recrystallized in cyclohexane.

Yield: 80%.
Melting point: 97° C.
Spectral characteristics:
Infrared: 1765 cm$^{-1}$:$\nu$ CO (O—CO—N)

Nuclear magnetic resonance: $\delta$=3.35 ppm, singlet, 3H, (N—CH$_3$) $\delta$=6.20 ppm, split triplet, 1H, —CH—CH$_2$ $\delta$=6.62 ppm, doublet, 1H, —CH=CH, J=15.9 Hz

EXAMPLE 9

3-METHYL-6-{3-[4-(2-METHOXYPHENYL)-1-PIPERAZINYL]-1-PROPENYL}BENZOXAZOLINONE

Using the procedure described in Example 8, but replacing 3-methyl-6-{3-[4-(3-trifluoromethylphenyl)-1-piperazinyl]-1-hydroxypropyl}benzoxazolinone by 3-methyl-6-{3-[4-(2-methoxyphenyl)-1-piperazinyl]-1-hydroxypropyl}benzoxazolinone, obtained in Example 6, the product of the title is obtained.

Recrystallization solvent: ethanol.
Yield: 80%.
Melting point: 151° C.
Spectral characteristics:
Infrared: 1760 cm$^{-1}$:$\nu$ CO (O—CO—N).

Nuclear magnetic resonance: $\delta$=3.38 ppm, singlet, 3H, N—CH$_3$; $\delta$=3.83 ppm, singlet, 3H, —OCH$_3$; $\delta$=6.19 ppm, split triplet, 1H, =CH—CH$_2$; $\delta$=6.60 ppm, doublet, 1H, CH=CH, J=16 Hz.

EXAMPLE 10

3-METHYL-6-{3-[4-(4-FLUOROPHENYL)-1-PIPERAZINYL]-1-PROPENYL}BENZOXAZOLINONE

Using the procedure described in Example 8, but replacing 3-methyl-6-{3-[4-(3-trifluoromethylphenyl)-1-piperazinyl]-1-hydroxypropyl}benzoxazolinone by 3-methyl-6-{3-[4-(4-fluorophenyl)-1-piperazinyl]-1-hydroxypropyl}benzoxazolinone, obtained in Example 7, the product of the title is obtained.

Melting point: 164° C.
Spectral characteristics:
Infrared: 1770 cm$^{-1}$:$\nu$ CO (O—CO—N).

Nuclear magnetic resonance: $\delta$=3.38 ppm, singlet, 3H, N—CH$_3$; $\delta$=6.20 ppm, split triplet, 1H, =CH—CH$_2$, J=16.1 Hz; $\delta$=6.55 ppm, doublet, 1H, —CH=CH, J=16.1 Hz.

EXAMPLE 11

3-METHYL-6-{3-[4-(3-TRIFLUOROMETHYLPHENYL)-1-PIPERAZINYL]PROPYL}BENZOXAZOLINONE (HYDROCHLORIDE)

STAGE A: 3-Methyl-6-{3-[4-(3-trifluoromethylphenyl)-1-piperazinyl]-1-propenyl}benzoxazolinone Obtained in Example 8.

STAGE B: 3-Methyl-6-{3-[4-(3-trifluoromethylphenyl)-1-piperazinyl]propyl}benzoxazolinone 0.01 mole of 3-methyl-6-{3-[4-(3-trifluoromethylphenyl)-1-piperazinyl]-1-propenyl}benzoxazolinone is dissolved in methanol in a 500-cm³ conical flask equipped with a three-way tap and a magnetic stirrer, and 0.5 g of Raney nickel is then added. The mixture is stirred under a hydrogen atmosphere at room temperature and at atmospheric pressure. After the theoretical amount of hydrogen has been absorbed, the reaction mixture is filtered and the filtrate is evaporated to dryness on a water bath under vacuum. The residue is taken up with water and acidified with hydrochloric acid, and the precipitate obtained is drained and recrystallized in ethanol.

Melting point: 234° C.
Spectral characteristics:
Infrared: 2540-2420 cm$^{-1}$:$\nu$ NH$^+$ (tertiary amine hydrochloride); 1780-1760 cm$^{-1}$:$\nu$ CO (O—CO—N).

Nuclear magnetic resonance: $\delta$=1.90 ppm, quintet, 2H, CH$_2$—CH$_2$—CH$_2$; $\delta$=2.67 ppm, complex, 8H, CH$_2$—CH$_2$ and piperazine; $\delta$=3.34 ppm, complex, 7H, N—CH$_3$ and piperazine.

EXAMPLE 12

3-METHYL-6-{3-[4-(2-METHOXYPHENYL)-1-PIPERAZINYL]PROPYL}BENZOXAZOLINONE (HYDROBROMIDE)

STAGE A: 3-Methyl-6-{3-[4-(2-methoxyphenyl)-1-piperazinyl]-1-propenyl}benzoxazolinone Obtained in Example 9.

STAGE B: 3-Methyl-6-{3-[4-(2-methoxyphenyl)-1-piperazinyl]propyl}benzoxazolinone 0.01 mole of 3-methyl-6-{3-[4-(2-methoxyphenyl)-1-piperazinyl]-1-propenyl}benzoxazolinone is dissolved in ethanol in a 500-cm³ flask equipped with a three-way tap and a magnetic stirrer, and 0.5 g of Raney nickel is then added. The mixture is stirred under hydrogen at room temperature and at atmospheric pressure. After the theoretical amount of hydrogen has been absorbed, the reaction medium is filtered and the filtrate is evaporated to dryness on a water bath under vacuum. The residue is taken up in absolute alcohol, a stream of gaseous hydrobromic acid is bubbled through until the amine hydrobromide has precipitated, and the product is drained and recrystallized in 95% strength alcohol.

Melting point: 222° C.
Spectral characteristics:
Infrared: 2660-2540 cm$^{-1}$:$\nu$ NH$^+$ (tertiary amine); 1765 cm$^{-1}$:$\nu$ CO (O—CO—N).

Nuclear magnetic resonance: $\delta$=2.40 ppm, quintet, 2H, CH$_2$—CH$_2$—CH$_2$ $\delta$=3.00 ppm, complex, 6H, CH$_2$—N and piperazine $\delta$=3.37 ppm, singlet, 3H, N—CH$_3$ $\delta$=3.55 ppm, complex, 6H, CH$_2$—CH$_2$—CH$_2$ and piperazine $\delta$=3.83 ppm, singlet, 3H, OCH$_3$

EXAMPLE 13

3-METHYL-6-{3-[4-(4-FLUOROPHENYL)-1-PIPERAZINYL]PROPYL}BENZOXAZOLINONE

STAGE A: 3-Methyl-6-{3-[4-(4-fluorophenyl)-1-piperazinyl]-1-propenyl}benzoxazolinone
Obtained in Example 10.

STAGE B: 3-Methyl-6-{3-[4-(4-fluorophenyl)-1-piperazinyl]propyl}benzoxazolinone 0.01 mole of 3-methyl-6-{3-[4-(4-fluorophenyl)-1-piperazinyl]-1-propenyl}benzoxazolinone is dissolved in ethyl acetate in a 500-cm$^3$ flask equipped with a three-way tap and a magnetic stirrer, and 0.5 g of Raney nickel is then added. The mixture is stirred under a hydrogen atmosphere at room temperature and atmospheric pressure. After the theoretical amount of hydrogen has been absorbed, the reaction medium is filtered and the filtrate is evaporated to dryness on a water bath under vacuum. The residue is crystallized in ethanol.

Melting point: 108° C.
Spectral characteristics:
Infrared: 1765 cm$^{-1}$:$\nu$ CO (O—CO—N).
Nuclear magnetic resonance: $\delta=1.88$ ppm, quintet, 2H, CH$_2$—CH$_2$—CH$_2$; $\delta=2.59$ ppm, complex, 8H, CH$_2$—CH$_2$—CH$_2$ and piperazine; $\delta=3.12$ ppm, triplet, 4H, piperazine; $\delta=3.40$ ppm, singlet, 3H, N—CH$_3$.

EXAMPLE 14

3-METHYL-6-{3-[4-(3-TRIFLUOROMETHYLPHENYL)-1-PIPERAZINYL]-2-METHYLPROPIONYL}BENZOXAZOLINONE 0.025 mole of 6-propionyl-3-methylbenzoxazolinone, described in French Patent No. 73/23,280, and 0.038 mole of 1-(3-trifluoromethylphenyl)piperazine are dissolved in 150 cm$^3$ of propanol in a 250-cm$^3$ ground-necked flask equipped with a reflux condenser and a magnetic stirrer. 0.038 mole of trioxymethylene and 1.5 cm$^3$ of concentrated hydrochloric acid are added. The mixture is heated to reflux for 72 hours. The precipitate formed is drained, washed with acetone, suspended in water and alkalinized with sodium hydroxide. The mixture is extracted several times with chloroform, the organic phases are combined, dried over calcium chloride, filtered and evaporated on a water bath under vacuum and the residue is recrystallized in propanol.

Yield: 74%.
Melting point: 92° C.
Spectral characteristics:
Infrared: 1780 cm$^{-1}$:$\nu$ CO (O—CO—N); 1670 cm$^{-1}$:$\nu$ CO (acyl).
Nuclear magnetic resonance: $\delta=1.23$ ppm, doublet, 3H, CH—CH$_3$, J=5.8 Hz; $\delta=2.72$ ppm, complex, 6H, CH—CH$_2$ and piperazine; $\delta=3.17$ ppm, triplet, 4H, piperazine; $\delta=3.41$ ppm, singlet, 3H, N—CH$_3$; $\delta=3.75$ ppm, complex, 1H, CH—CH$_3$.

EXAMPLE 15

3-METHYL-6-{3-[4-(2-METHOXYPHENYL)-1-PIPERAZINYL]-2-METHYLPROPIONYL}BENZOXAZOLINONE

STAGE A: 3-Methyl-6-(2-methylenepropionyl)benzoxazolinone 0.01 mole of 3-methyl-6-propionylbenzoxazolinone and 0.04 mole of bis(dimethylamino)methane are introduced into a 150-cm$^3$ ground-necked flask equipped with a reflux condenser and a magnetic stirrer. 15 cm$^3$ of acetic anhydride are added dropwise and the mixture is heated to 100° C. for 5 hours. After being cooled, the reaction mixture is poured into 5 volumes of ice-cold water. The mixture is acidified and stirred for one hour, and the product is drained, washed with water to neutrality, dried and recrystallized in hexane.

Yield: 66%.
Melting point: 82° C.

STAGE B: 3-Methyl-6-{3-[4-(2-methoxyphenyl)-1-piperazinyl]-2-methylpropionyl}benzoxazolinone 100 cm$^3$ of anhydrous acetone, 0.01 mole of 3-methyl-6-(2-methylenepropionyl)benzoxazolinone and 0.01 mole of 1-(2-methoxyphenyl)piperazine are introduced successively into a 250-cm$^3$ ground-necked flask equipped with a reflux condenser and a magnetic stirrer. The mixture is brought to reflux for 6 hours and allowed to cool. The product is drained: the product of the title is obtained.

Yield: 82%.
Melting point: 156° C.
Spectral characteristics:
Infrared: 1785 cm$^{-1}$:$\nu$ CO (O—CO—N); 1660 cm$^{-1}$:$\nu$ CO (acyl).
Nuclear magnetic resonance: $\delta=1.24$ ppm, doublet, 3H, CH—CH$_3$; $\delta=2.60$ ppm, complex, 6H, CH—CH$_2$ and piperazine; $\delta=3.00$ ppm, triplet, 4H, piperazine; $\delta=3.39$ ppm, singlet, 3H, N—CH$_3$; $\delta=3.63$ ppm, complex, 1H, CH—CH$_3$; $\delta=3.84$ ppm, singlet, 3H, OCH$_3$.

EXAMPLE 16

(±)-ERYTHRO-3-METHYL-6-{3-[4-(3-TRIFLUOROMETHYLPHENYL)-1-PIPERAZINYL]-1-HYDROXY-2-METHYLPROPYL}BENZOXAZOLINONE 0.01 mole of 3-methyl-6-{3-[4-(3-trifluoromethylphenyl)-1-piperazinyl]-2-methylpropionyl}benzoxazolinone, obtained in Example 14, is dissolved in ethanol in a 250-cm$^3$ autoclave, and 0.5 g of palladinized charcoal (10% palladium) is added. The mixture is hydrogenated under 50 atmospheres of hydrogen for 8 hours at a temperature in the region of 70° C. After the mixture is cooled, the hydrogen is removed, the mixture is filtered and the filtrate is evaporated on a water bath under vacuum. The residue is recrystallized in dilute ethanol.

Yield: 67%.
Melting point: 120° C.
Spectral characteristics:
Infrared: 3210 cm$^{-1}$:$\nu$ OH (alcohol); 1765 cm$^{-1}$:$\nu$ CO (O—CO—N).
Nuclear magnetic resonance: $\delta=0.8$ ppm, doublet, 3H, CH—CH$_3$, J=5.7 Hz; $\delta=4.89$ ppm, doublet, 1H, CH—OH, J=erythro =2.5 Hz.

EXAMPLE 17

(±)-ERYTHRO-3-METHYL-6-{3-[4-(2-METHOXYPHENYL)-1-PIPERAZINYL]-1-HYDROXY-2-METHYLPROPYL}-BENZOXAZOLINONE

Using the procedure described in Example 16, but hydrogenating 3-methyl-6-{3-[4-(2-methoxyphenyl)-1-piperazinyl]-2-methylpropionyl}benzoxazolinone, obtained in Example 15, (hydrogenation solvent: dioxane), the product of the title is obtained.

Yield: 70%.
Melting point: 114° C.
Spectral characteristics:
Infrared: 3185 cm$^{-1}$:$\nu$ OH (secondary alcohol); 1765 cm$^{-1}$:$\nu$ CO (O—CO—N).

Nuclear magnetic resonance: δ=0.77 ppm, doublet, 3H, CH—CH$_3$, J=5.6 Hz; δ=3.40 ppm, singlet, 3H, N—CH$_3$; δ=3.87 ppm, singlet, 3H, O—CH$_3$; δ=4.86 ppm, doublet, 1H, CH—OH, J erythro=2.7 Hz.

EXAMPLE 18

(±)-THREO-3-METHYL-6-{3-[4-(3-TRI-FLUOROMETHYLPHENYL)-1-PIPERAZINYL]-1-HYDROXY-2-METHYLPROPYL}BENZOX-AZOLINONE 0.01 mole of 3-methyl-6-{3-[4-(3-trifluoromethyl-phenyl)-1-piperazinyl]-2-methylpropionyl}benzoxazolinone, obtained in Example 14, is placed in 25 cm$^3$ of methanol. 0.02 mole of sodium borohydride is added in small portions and with stirring. Stirring is maintained for 2 hours at room temperature. The solvent is evaporated off on a water bath under vacuum. The residue is taken up with water and extracted with chloroform. The organic phase is dried over calcium chloride, filtered and evaporated on a water bath under vacuum. A mixture of enantiomers is obtained, from which the preponderant threo derivative is isolated by chromatography on silica get (eluant: methylene chloride/acetone, 8.5:1.5).

Yield: 30%.
Melting point: 80° C.
Spectral characteristics:
Infrared: 3110 cm$^{-1}$:ν OH (secondary alcohol); 1770 cm$^{-1}$:ν CO (O—CO—N) benzoxazolinone.
Nuclear magnetic resonance: δ=0.58 ppm, doublet, 3H, CH—CH$_3$, J=5.8 Hz; δ=4.40 ppm, doublet, 1H, CH—OH, J erythro=8.8 Hz.

EXAMPLE 19

(±)-THREO-3-METHYL-6-{3-[4-(2-METHOXY-PHENYL)-1-PIPERAZINYL]-1-HYDROXY-2-METHYLPROPYL}BENZOXAZOLINONE

Using the procedure described in Example 18, but employing 3-methyl-6-{3-[4-(2-methoxyphenyl)-1-piperazinyl]-2-methylpropionyl}benzoxazolinone, obtained in Example 15, as starting material, the product of the title is obtained. Elution solvent: chloroform/acetone, 4:1.

Yield: 32%.
Melting point: 64° C.
Spectral characteristics:
Infrared: 3210 cm$^{-1}$:ν OH (secondary alcohol); 1765 cm$^{-1}$:ν CO (O—CO—N) benzoxazolinone.
Nuclear magnetic resonance: δ=0.58 ppm, doublet, 3H, CH—CH$_3$, J=6 Hz; δ=3.38 ppm, singlet, 3H, N—CH$_3$; δ=3.91 ppm, singlet, 3H, O—CH$_3$; δ=4.44 ppm, doublet, 1H, CH—OH, J=threo=8.95 Hz.

EXAMPLE 20

3-METHYL-6-{3-[4-(3-TRIFLUOROMETHYL-PHENYL)-1-PIPERAZINYL]-2-METHYL-1-PROPENYL}BENZOXAZOLINONE 0.01 mole of 3-methyl-6-{3-[4-(3-trifluoromethyl-phenyl)-1-piperazinyl]-2-methyl-1-hydroxypropyl}ben-zoxazolinone, obtained in Example 16, is dissolved in 100 cm$^3$ of 47% strength hydrobromic acid in a 250-cm$^3$ flask equipped with a magnetic stirrer. The mixture is heated on a water bath to 40° C. and magnetic stirring is continued for 2 hours. The precipitate formed is drained, washed with acetone, suspended in water and alkalinized. The mixture is extracted with chloroform, the organic phases are dried over calcium chloride, filtered and evaporated to dryness on a water bath under vacuum and the product is recrystallized in hexane.

Yield: 71%.
Melting point: 92° C.
Spectral characteristics:
Infrared: 1790-1770 cm$^{-1}$:ν CO (O—CO—N).
Nuclear magnetic resonance: δ=1.95 ppm, singlet, 3H, CH—CH$_3$; δ=3.40 ppm, singlet, 3H, N—CH$_3$; δ=6.45 ppm, singlet, 1H, —CH=.

EXAMPLE 21

3-METHYL-6-{3-[4-(2-METHOXYPHENYL)-1-PIPERAZINYL]-2-METHYL-1-PROPENYL}BEN-ZOXAZOLINONE

Using the procedure described in Example 20, but employing 3-methyl-6-{3-[4-(2-methoxyphenyl)-1-piperazinyl]-2-methyl-1-hydroxypropyl}benzoxazolinone, as starting material, the product of the title is obtained.

Recrystallization solvent: ethanol.
Yield: 82%.
Melting point: 148° C.
Spectral characteristics:
Infrared: 1780 cm$^{-1}$:ν CO (O—CO—N).
Nuclear magnetic resonance: δ=1.90 ppm, singlet, 3H, C—CH$_3$; δ=3.78 ppm, singlet, 3H, N—CH$_3$; δ=3.85 ppm, singlet, 3H, O—CH$_3$; δ=6.50 ppm, singlet, 1H, —CH=.

EXAMPLE 22

3-METHYL-6-{3-[4-(3-TRIFLUOROMETHYL-PHENYL)-1-PIPERAZINYL]-2-METHYL-PROPYL}BENZOXAZOLINONE (HYDROCHLORIDE)

0.01 mole of 3-methyl-6-{3-[4-(3-trifluoromethyl-phenyl)-1-piperazinyl]-2-methyl-1-propenyl}benzox-azolinone, obtained in Example 20, is dissolved in absolute ethanol in a 500-cm$^3$ flask equipped with a three-way tap and a magnetic stirrer. 0.5 g of Raney nickel is added and the mixture is stirred under a hydrogen atmosphere at room temperature and atmospheric pressure. After the theoretical amount of hydrogen has been absorbed, the reaction medium is filtered and the filtrate is evaporated to dryness on a water bath under vacuum. The residue is taken up with water and acidified and the product is drained and recrystallized in ethanol.

Yield: 80%.
Melting point: 261° C.
Spectral characteristics:
Infrared: 2520-2490 cm$^{-1}$:ν NH$^+$ (Cl$^-$ of tertiary amine); 1765 cm$^{-1}$:ν (CO) (O—CO—N).
Nuclear magnetic resonance (solvent DMSO): δ=0.94 ppm, doublet, 3H, CH$_3$—CH, J=6.1 Hz; δ=3.37 ppm, singlet, 3H, N—CH$_3$.

EXAMPLE 23

3-METHYL-6-{3-[4-(2-METHOXYPHENYL)-1-PIPERAZINYL]-2-METHYLPROPYL}BENZOX-AZOLINONE 0.01 mole of 3-methyl-6-{3-[4-(2-methoxyphenyl)-1-piperazinyl]-2-methyl-1-propenyl}benzoxazolinone is dissolved in absolute ethanol in a 500-cm$^3$ flask equipped with a three-way tap and a magnetic stirrer. 0.5 g of Raney nickel is added and the mixture is stirred under a hydrogen atmosphere at room temperature and atmospheric pressure. After the theoretical amount of hydrogen has been absorbed, the reaction medium is filtered, the filtrate is evaporated to dryness on a water bath under vacuum and the residue is recrystallized in cyclohexane.

Yield: 78%.
Melting point: 105° C.
Spectral characteristics:
Infrared: 1760 cm$^{-1}$:$\nu$ CO (O—CO—N).
Nuclear magnetic resonance (solvent DMSO): $\delta$=0.88 ppm, doublet, 3H, CH—CH$_3$, J=5.6 Hz; $\delta$=3.37 ppm, singlet, 3H, N—CH$_3$; $\delta$=3.84 ppm, singlet, 3H, O—CH$_3$.

EXAMPLE 24

3-METHYL-6-{3-[4-(2-METHOXYPHENYL)-1-PIPERAZINYL]-2-METHYLPROPYL}BENZOXAZOLINONE

STAGE A: 3-Methyl-6-(3-bromo-2-methylpropionyl)benzoxazolinone 0.05 mole of 3-methyl-6-(2-methylenepropionyl)benzoxazolinone, obtained in Example 15, Stage A, is dissolved with stirring in 150 cm$^3$ of acetone in a 250-cm$^3$ flask. A stream of hydrobromic acid is bubbled into the solution and stirring is maintained for one hour. The mixture is filtered, the filtrate is evaporated on a water bath under vacuum and the residue is recrystallized in absolute ethanol.

Yield: 85%.
Melting point: 127° C.

STAGE B: 3-Methyl-6-(3-bromo-2-methylpropyl)benzoxazolinone 0.03 mole of 3-methyl-6-(3-bromo-2-methylpropionyl)benzoxazolinone is dissolved in 0.3 mole of trifluoroacetic acid in a 150-cm$^3$ flask. 0.066 mole of triethylsilane is added dropwise and with cooling. Stirring is continued for 24 hours at room temperature. The reaction mixture is poured into 5 volumes of ice-cold water. The precipitate obtained is drained, washed with water until the washing liquors are neutral, dried and recrystallized in cyclohexane.

Yield: 67%.
Melting point: 70° C.

STAGE C: 3-Methyl-6-{3-[4-(2-methoxyphenyl)-1-piperazinyl]-2-methylpropyl}benzoxazolinone 0.02 mole of 3-methyl-6-(3-bromo-2-methylpropyl)benzoxazolinone, obtained in Stage B, is dissolved in anhydrous dioxane in a 250-cm$^3$ ground-necked flask equipped with a reflux condenser. 0.02 mole of 1-(2-methoxyphenyl)piperazine and 0.02 mole of triethylamine dissolved in dioxane are added with magnetic stirring. The mixture is brought to reflux for 48 hours. The precipitate formed is drained while hot and the filtrate is evaporated on a water bath under vacuum. The residue is taken up 500 cm$^3$ of water and alkalinized. The mixture is extracted with chloroform and the organic phases are dried over calcium chloride. The organic phases are filtered and the solvent is evaporated off on a water bath under vacuum. The residue is recrystallized in cyclohexane. The physicochemical characteristics of this product are identical in all respects to those of the product obtained in Example 23.

EXAMPLE 25

3-METHYL-6-{3-[4-(2-METHOXYPHENYL)-1-PIPERAZINYL]PROPYL}BENZOXAZOLINONE

STAGE A: 6-(3-Bromopropionyl)-3-methylbenzoxazolinone 6.02 ml (0.078 mole) of dimethylformamide are introduced dropwise and with stirring into a ground-necked flask containing 37.4 g (0.28 mole) of anhydrous aluminum chloride.

The flask is fitted with a reflux condenser and brought in an oil bath to a temperature in the region of 40°–45° C. 0.04 mole of 3-methylbenzoxazolinone and 0.044 mole of 3-bromopropionic acid chloride are introduced. The mixture is heated to a temperature in the region of 75° C. for 2 h 30 min.

After the reaction mixture is cooled, it is poured into 300 g of ice, acidified with concentrated hydrochloric acid and stirred for 1 h 30 min.

The precipitate obtained is drained, washed with water and dried. The product is recrystallized in dioxane.

Yield: 85%.
Melting point: 184° C. (decomposition).
Spectral characteristics:
Infrared: 1765 cm$^{-1}$:$\nu$ CO (O—CO—N); 1660 cm$^{-1}$:$\nu$ CO (keto).
Nuclear magnetic resonance (solvent DMSO): $\delta$=3.44 ppm, singlet, 3H, N—CH$_3$.

STAGE B: 6-(3-Bromopropyl)-3-methylbenzoxazolinone 0.02 mole of 6-(3-bromopropionyl)-3-methylbenzoxazolinone, obtained in the preceding stage, is dissolved in 0.2 mole of trifluoroacetic acid in a ground-necked flask. 0.044 mole of triethylsilane is added dropwise and while cooling. A calcium chloride guard tube is fitted and stirring is continued for 72 hours. The reaction medium is then poured into ice-cold water and the precipitate obtained is drained, dried and recrystallized in hexane.

Yield: 85%.
Melting point: 83°–84° C.
Spectral characteristics:
Infrared: 1780 cm$^{-1}$:$\nu$ CO (O—CO—N).
Nuclear magnetic resonance (solvent DMSO): $\delta$=2.14 ppm, multiplet, 2H—CH$_2$—CH$_2$ Br; $\delta$=2.68 ppm, triplet, 2H, —CH$_2$—(CH$_2$)$_2$ Br.

STAGE C: 3-Methyl-6-{3-[4-(2-methoxyphenyl)-1-piperazinyl]propyl}benzoxazolinone The procedure is as described in Example 24, Stage C, replacing 3-methyl-6-(3-bromo-2-methylpropyl)benzoxazolinone by 3-methyl-6-(3-bromopropyl)benzoxazolinone, obtained in the preceding stage. The product of the title is obtained.

Recrystallization solvent: hexane.
Spectral characteristics:
Infrared: 1760 cm$^{-1}$:$\nu$ CO (O—CO—N).
Nuclear magnetic resonance (solvent DMSO): $\delta$=3.38 ppm, singlet, 3H N—CH$_3$; $\delta$=3.83 ppm, singlet, 3H O—CH$_3$.

EXAMPLE 26

6-{3-[4-(2-METHOXYPHENYL)-1-PIPERAZINYL]PROPYL}BENZOXAZOLINONE

STAGE A: 6-(3-Bromopropionyl)benzoxazolinone

This procedure is as in Example 25, Stage A, replacing 3-methylbenzoxazolinone by benzoxazolinone; the expected product is obtained.
Yield: 70%.
Melting point: 162° C. (decomposition).
Spectral characteristics:
Infrared: 3340, 3100 cm$^{-1}$:$\nu$ NH; 1755 cm$^{-1}$:$\nu$ CO (O—CO—N); 1655 cm$^{-1}$:$\nu$ CO (ketone).
Nuclear magnetic resonance (solvent DMSO):
$\delta$=3.41 to 4.00 ppm, multiplet, 4H CH$_2$—CH$_2$;
$\delta$=11.71 ppm, broad signal, 1H, NH, exchangeable.
STAGE B: 6-(3-Bromopropyl)benzoxazolinone
The procedure is as described in Example 25, Stage B, replacing 3-methyl-6-(3-bromopropionyl)benzoxazolinone by 6-(3-bromopropionyl)benzoxazolinone, obtained in Stage A.
Yield: 80%.
Melting point: 131°–132° C. (decomposition).
Spectral characteristics:
Infrared: 3300, 3040 cm$^{-1}$:$\nu$ NH; 1775 cm$^{-1}$:$\nu$ CO (O—CO—N).
Nuclear magnetic resonance (solvent DMSO):
$\delta$=2.12 ppm, multiplet, 2H, CH$_2$—CH$_2$—CH$_2$ Br;
$\delta$=2.66 ppm, triplet, 2H, CH$_2$—CH$_2$—CH$_2$ Br; $\delta$=3.46 ppm, multiplet, 2H, CH$_2$—CH$_2$—CH$_2$ Br; $\delta$=9.40 ppm, broad signal, 1H, exchangeable, NH.
STAGE C: 6-{3-[4-(2-Methoxyphenyl)-1-piperazinyl]propyl}benzoxazolinone
Using the procedure described in Example 25, Stage C, and replacing 3-methyl-6-(3-bromopropyl)benzoxazolinone by 6-(3-bromopropyl)benzoxazolinone, the expected product is obtained.
Yield: 70%.
Spectral characteristics:
Infrared: 3200, 2400 cm$^{-1}$:$\nu$ NH and $\nu$ CH; 1765 cm$^{-1}$:$\nu$ CO (O—CO—N).
Nuclear magnetic resonance (solvent DMSO):
$\delta$=3.80 ppm, singlet, O—CH$_3$.

EXAMPLES 27 AND 28

By replacing 1-(2-methoxyphenyl)piperazine in Examples 25 and 26 by 1-(4-4-fluorophenyl)piperazine, the following are obtained:

3-METHYL-6-{3-[4-(4-FLUOROPHENYL)-1-PIPERAZINYL]PROPYL}BENZOXAZOLINONE (EXAMPLE 27)

6-{3-[4-(4-FLUOROPHENYL)-1-PIPERAZINYL]-PROPYL}BENZOXAZOLINONE (EXAMPLE 28)

EXAMPLES 29 AND 30

By replacing 1-(2-methoxyphenyl)piperazine in Examples 25 and 26 by 1-(3-trifluoromethylphenyl)piperazine, the following are obtained:

3-METHYL-6-{3-[4-(3-TRIFLUOROMETHYL-PHENYL)-1-PIPERAZINYL]PROPYL}BENZOXAZOLINONE (EXAMPLE 29)

6-{3-[4-(3-TRIFLUOROMETHYLPHENYL)-1-PIPERAZINYL]PROPYL}BENZOXAZOLINONE (EXAMPLE 30)

EXAMPLE 31

3-METHYL-6-{3-[4-(2-PYRIDYL)-1-PIPERAZINYL]-1-OXOPROPYL}BENZOXAZOLINONE

Using the procedure described in Example 1, but replacing 1-(3-trifluoromethylphenyl)piperazine by 1-(2-pyridyl)piperazine, the product of the title is obtained.

EXAMPLE 32

3-METHYL-6-[3-(4-BENZYL-1-PIPERAZINYL)-1-OXOPROPYL]BENZOXAZOLINONE

Using the procedure described in Example 1, but replacing 1-(3-trifluoromethylphenyl)piperazine by 1-benzylpiperazine, the product of the title is obtained.

EXAMPLE 33

3-METHYL-6-{3-[4-(6-METHYL-2-PYRIDYL)-1-PIPERAZINYL]-1-OXOPROPYL}BENZOXAZOLINONE

Using the procedure described in Example 1, but replacing 1-(3-trifluoromethylphenyl)piperazine by 1-(6-methyl-2-pyridyl)piperazine, the product of the title is obtained.

EXAMPLE 34

3-METHYL-6-{3-[4-(2-PYRIMIDINYL)-1-PIPERAZINYL]-1-HYDROXYPROPYL}BENZOXAZOLINONE

Using the procedure described in Example 5, but replacing 3-methyl-6-{3-[4-(3-trifluoromethylphenyl)-1-piperazinyl]-1-oxopropyl}benzoxazolinone by 3-methyl-6-{3-[4-(2-pyrimidinyl)-1-piperazinyl]-1-oxopropyl}benzoxazolinone, obtained in Example 4, the product of the title is obtained.

EXAMPLE 35

3-METHYL-6-{3-[4-(2-PYRIMIDINYL)-1-PIPERAZINYL]-1-PROPENYL}BENZOXAZOLINONE

Using the procedure described in Example 8, but replacing 3-methyl-6-{3-[4-(3-trifluoromethylphenyl)-1-piperazinyl]-1-hydroxypropyl}benzoxazolinone by 3-methyl-6-{3-[4-(2-pyrimidinyl)-1-piperazinyl]-1-hydroxypropyl}benzoxazolinone, obtained in Example 34, the product of the title is obtained.

EXAMPLE 36

3-METHYL-6-{3-[4-(6-METHYL-2-PYRIDYL)-1-PIPERAZINYL]-1-HYDROXYPROPYL}BENZOXAZOLINONE

Using the procedure described in Example 5, but replacing 3-methyl-6-{3-[4-(3-trifluoromethylphenyl)-1-piperazinyl]-1-oxopropyl}benzoxazolinone by 3-methyl-6-{3-[4-(6-methyl-2-pyridyl)-1-piperazinyl]-1-oxopropyl}benzoxazolinone, obtained in Example 33, the product of the title is obtained.

EXAMPLE 37

3-METHYL-6-{3-[4-(6-METHYL-2-PYRIDYL)-1-PIPERAZINYL]-1-PROPENYL}BENZOXAZOLINONE

Using the procedure described in Example 8, but replacing 3-methyl-6-{3-[4-(3-trifluoromethylphenyl)-1-piperazinyl]-1-hydroxypropyl}benzoxazolinone by 3-methyl-6-{3-[4-(6-methyl-2-pyridyl)-1-piperazinyl]-1-hydroxypropyl}benzoxazolinone, obtained in Example 36, the product of the title is obtained.

EXEMPLE 38

3-METHYL-6-[3-(4-PHENYL-1-PIPERAZINYL)-1-OXOPROPYL]BENZOXAZOLINONE

Using the procedure described in Example 1, but replacing 1-(3-trifluoromethylphenyl) piperazine by 1-phenyl piperazine, the product of the title is obtained.

EXAMPLE 39

3-METHYL-6-[3-(4-PHENYL-1-PIPERAZINYL)-1-HYDROXYPROPYL]BENZOXAZOLINONE

Using the procedure described in Example 5 but replacing 3-Methyl-6-{3-[4-(3-trifluoromethylphenyl)-1-piperazinyl]-1-oxopropyl}benzoxazolinone by 3-Methyl-6-[3-(4-phenyl-1-piperazinyl)-1-oxopropyl]benzoxazolinone, obtained in example 38, the product of the title is obtained.

EXAMPLE 40

3-METHYL-6-[3-(4-PHENYL-1-PIPERAZINYL)-PROPYL]BENZOXAZOLINONE

Using the procedure described in example 25 but replacing 1-(2-methoxyphenyl)piperazine by 1-phenyl-piperazine, the product of the title is obtained.

EXAMPLE 41

6-[3-(4-PHENYL-1-PIPERAZINYL)PROPYL]BENZOXAZOLINONE

Using the procedure described in example 26 but replacing 1-(2-methoxyphenyl) piperazine by 1-phenyl piperazine, the product of the title is obtained.

EXAMPLE 42

3-METHYL-6-{3-[4-(2-PYRIDYL)-1-PIPERAZINYL]-1-HYDROXYPROPYL}BENZOXAZOLINONE

Using the procedure described in example 5 but replacing 3-Methyl-6-{3-[4-(3-trifluoromethylphenyl)-1-piperazinyl]-1-oxopropyl}benzoxazolinone by 3-methyl-6-{3-[4-(2-pyridyl)-1-piperazinyl]-1-oxopropyl}benzoxazolinone, obtained in example 31, the product of the title is obtained.

EXAMPLE 43

3-METHYL-6-{3-[4-(2-PYRIDYL)-1-PIPERAZINYL]PROPYL}BENZOXAZOLINONE

Using the product described in example 25 but replacing 1-(2-methoxyphenyl) piperazine by 1-(2-pyridyl)-piperazine, the product of the title is obtained.

EXAMPLE 44

6-{3-[4-(2-PYRIDYL)-1-PIPERAZINYL]PROPYL}BENZOXAZOLINONE

Using the procedure described in example 26 but replacing 1-(2-methoxyphenyl) piperazine by 1-(2-pyridyl) piperazine, the product of the title is obtained.

PHARMACOLOGICAL STUDY OF THE DERIVATIVES OF THE INVENTION

EXAMPLE 45

STUDY OF THE ACUTE TOXICITY

The acute toxicity was assessed after the oral administration of a dose of 1000 mg/kg$^{-1}$ to batches of 8 mice (26±2 grams). The animals were observed at regular intervals during the first day, and daily during the 2 weeks following the treatment.

It is apparent that the toxicity of the derivatives of the invention varies very greatly according to their structure. Those for which X and Y simultaneously denote an oxygen atom have very low toxicity (0% mortality). For the other derivatives, the percentage mortality obtained varies greatly according to the nature of X, Y and Ar.

EXAMPLE 46

STUDY OF THE ANALGESIC ACTIVITY

The activity against pain was investigated in mice (23–25 g) according to a protocol derived from the technique described by Siegmund (Siegmund E. A., R. A. Cadmus & Golu, J. Pharm. Exp. Ther. 119, 1874, 1957). The mice, randomized in batches of 12 animals, received the treatment orally (excipient for the controls) 1 hour before the intraperitoneal injection of a 0.02% strength aqueous-alcoholic solution of phenyl-p-benzoquinone (Sigma). The writhing movements are counted between the 5th and 10th minute after injection.

The percentage activity obtained was evaluated for each dose (% decrease in the number of writhing movements in the treated animals relative to the controls). An $ED_{50}$, the dose producing a 50% activity, was determined for each product.

It was apparent that some compounds of the invention possess a very advantageous analgesic activity.

Thus, the $ED_{50}$ of the compound of Example 3 is in the region of 2 mg.kg$^{-1}$; the $ED_{50}$ of Example 2 is in the region of 5 mg.kg$^{-1}$.

By way of comparison, the administration of a dose of 100 mg.kg$^{-1}$ of the derivatives of French Patent No. 73/23,280 produced a percentage analgesic effect—in a comparable test—of the order of 25 to 60%, and the compound of French Patent No. 80/20,861, the analgesic activity of which is the most advantageous, had an $ED_{50}$ of 9 mg.kg$^{-1}$ in this same Siegmund test, that is to say 4.5 times as large as that of the most advantageous product of the present invention.

EXAMPLE 47

STUDY OF THE ANTI-INFLAMMATORY ACTIVITY

The anti-inflammatory potential of the compounds was investigated on a model of acute inflammation induced by the subcutaneous injection of a solution of carrageenan into the rat hind foot, according to a technique based on the method of Winter, C. A., E. A. Risley and G. N. Nuss (Proc. Soc. Exp. Med. 111, 554, 1962). The rats (100–120 g), randomized in batches of 8, were treated (including the controls, which receive excipient) 1 hour before the local injection of a 0.5% strength suspension of carrageenan (Sigma type IV; 0.1 ml per rat). The edema is determined 3 hours after injection, by plethysmometric measurement (Ugo Basile water plethysmometer) of the volume of each of the hind feet (edema=volume inflamed foot - volume non-inflamed foot).

It is apparent that the products of the invention have no activity in this test, or a very low activity. In comparison, the products of French Patent No. 73/23,280 possess an anti-inflammatory activity.

EXAMPLE 48

PHARMACEUTICAL COMPOSITION:TABLET

Tablets containing 20 mg of 3-methyl-6-{3-[4-(4-fluorophenyl)-1-piperazinyl]-1-oxopropyl}benzoxazolinone.

Preparation formula for 1000 tablets.

| | |
|---|---|
| 3-Methyl-6-{3-[4-(4-fluorophenyl)-1-piperazinyl]-1-oxopropyl}benzoxazolinone | 20 g |
| Wheat starch | 15 g |
| Corn starch | 15 g |
| Lactose | 65 g |
| Magnesium stearate | 2 g |
| Silica | 1 g |
| Hydroxypropyl cellulose | 2 g |

We claim:

1. A compound selected from those of the formula (I):

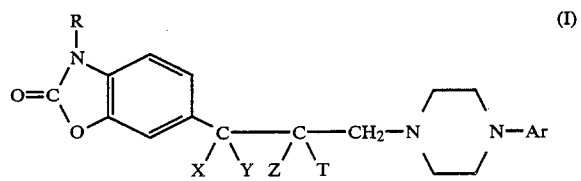

in which:
X denotes a hydrogen atom,
Y denotes a hydrogen atom or a hydroxyl group or alternatively X and Y together denote an oxygen atom,
T denotes a hydrogen atom or a lower alkyl group,
Z denotes a hydrogen atom or alternatively Z forms a $\pi$ bond with Y, in which case X denotes a hydrogen atom,
R denotes a hydrogen atom or a lower alkyl group,
Ar denotes an phenyl or heteroaryl, having 4–8 C and 1 or 2 N, O, or S atoms, or (lower alkyl)aryl group, which groups may be substituted with a halogen atom or a lower alkyloxy or alkyl group, which itself may be substituted with one or more halogen atoms,
an enantiomer, epimer or diastereoisomer thereof as well as an addition salt of any of the foregoing with a pharmaceutically acceptable acid.

2. A compound as claimed in claim 1, in which X and Y together simultaneously denote an oxygen atom.

3. A compound as claimed in claim 1, in which X denotes a hydrogen atom and Y a hydroxyl group.

4. A compound as claimed in claim 1, in which X and Y each simultaneously denote a hydrogen atom.

5. A compound as claimed in claim 1, in which Y forms a bond with Z.

6. A compound as claimed in claim 1, in which Ar denotes the phenyl group.

7. A compound as claimed in claim 1, in which Ar denotes the phenyl group, substituted with a halogen atom or a lower alkoxy group or a trifluoromethyl group.

8. A compound as claimed in claim 1, in which Ar denotes the 2-pyridyl group or the 2-pyrimidinyl group.

9. A compound as claimed in claim 1, which is 3-methyl-6-{3-[4-(4-fluorophenyl)-1-piperazinyl]-1-oxopropyl}benzoxazolinone or its addition salts with a pharmaceutically acceptable acid.

10. A compound as claimed in claim 1, which is 3-methyl-6-{3-[4-(2-methoxyphenyl)-1-piperazinyl]-1-oxopropyl}benzoxazolinone or its addition salts with a pharmaceutically acceptable acid.

11. A pharmaceutical composition useful for alleviation of pain containing, as active principle, an effective analgesic amount of at least one compound as claimed in claim 1, in combination with one or more pharmaceutically acceptable, non-toxic, inert vehicles or excipients.

12. A method for treating a living animal body afflicted with pain comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,960,778

DATED : Oct. 2, 1990

INVENTOR(S) : Daniel Lesieur, Nourddine Abdellatifi, Hocine Aichaoui, Jacqueline Bonnet It is certified that error appears in the above-identified patent and that said Letters Patent is hereby corrected as shown below:

Column 8, line 64; "driver" should read -- dried --.

Column 15, approximate line 23; "get" should read -- gel --.

Column 23, line 40; "an" should read -- a --.

Column 24, line 4; "thereof as" should read -- thereof, as --.

Signed and Sealed this

Fifth Day of May, 1992

Attest:

DOUGLAS B. COMER

Attesting Officer

Acting Commissioner of Patents and Trademarks